US008735149B2

(12) United States Patent
Reubinoff et al.

(10) Patent No.: US 8,735,149 B2
(45) Date of Patent: May 27, 2014

(54) MOTOR NEURONS DEVELOPED FROM STEM CELLS

(75) Inventors: Benjamin Reubinoff, Doar Na Haela (IL); Etti Ben Shushan, Jerusalem (IL); Michal Aharonowiz, Modiin (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 139 days.

(21) Appl. No.: 12/935,427

(22) PCT Filed: Apr. 5, 2009

(86) PCT No.: PCT/IL2009/000367
§ 371 (c)(1),
(2), (4) Date: Sep. 29, 2010

(87) PCT Pub. No.: WO2009/122413
PCT Pub. Date: Oct. 8, 2009

(65) Prior Publication Data
US 2011/0091927 A1    Apr. 21, 2011

Related U.S. Application Data

(60) Provisional application No. 61/064,854, filed on Mar. 31, 2008.

(51) Int. Cl.
*C12N 5/00* (2006.01)
*C12N 5/02* (2006.01)
*C12N 5/071* (2010.01)

(52) U.S. Cl.
USPC ........... 435/325; 435/366; 435/377; 435/384; 435/404

(58) Field of Classification Search
None
See application file for complete search history.

(56) References Cited

U.S. PATENT DOCUMENTS

2004/0224887 A1* 11/2004 Jessel et al. .................. 514/12
2006/0171935 A1*  8/2006 Abeliovich et al. ........ 424/93.21

FOREIGN PATENT DOCUMENTS

| WO | 02/086106 A1 | 10/2002 |
| WO | 2004/090110 A2 | 10/2004 |
| WO | WO 2004090110 A2 * | 10/2004 |
| WO | 2006/095175 A1 | 9/2006 |

OTHER PUBLICATIONS

Crawford et al. Developmental Dynamics, vol. 236, No. 3, Mar. 2007, pp. 886-892.*
Hu, et al., "Human oligodendrocytes from embryonic stem cells: conserved SHH signaling networks and divergent FGF effects", Development, vol. 136, pp. 1443-1452, (2009).
Briscoe, et al., "Regulatory pathways linking progenitor patterning, cell fates and neurogenesis in the ventral neural tube", Phil. Trans. R. Soc. B, vol. 363, pp. 57-70, (2008).
Cunliffe, "Histone deacetylase 1 is required to repress Notch target gene expression during zebrafish neurogenesis and to maintain the production of motoneurones in response to hedgehog signalling", Development, vol. 131, No. 12, pp. 2983-2995, (2004).
Givogri, et al., "Central Nervous System Myelination in Mice with Deficient Expression of Notch1 Receptor", Journal of Neuroscience Research, vol. 67, pp. 309-320, (2002).
Crawford, et al., "The Notch Response Inhibitor DAPT Enhances Neuronal Differentiation in Embryonic Stem Cell-Derived Embryoid Bodies Independently of Sonic Hedgehog Signaling", Developmental Dynamics, vol. 236, pp. 886-892, (2007).
Christou, et al., "Embryonic stem cells and prospects for their use in regenerative medicine approaches to motor neurone disease", Neuropathology and Applied Neurobiology, vol. 33, pp. 485-498, (2007).
Fortini, "γ-Secretase-Mediated Proteolysis in Cell-Surface-Receptor Signalling", Nature Reviews: Molecular Cell Biology, vol. 3, pp. 673-684, (2002).
Lee, et al., "Directed Differentiation and Transplantation of Human Embryonic Stem Cell-Derived Motoneurons", Stem Cells, vol. 25, pp. 1931-1939, (2007).
Dovey, et al., "Functional gamma-secretase inhibitors reduce beta-amyloid peptide levels in brain", Journal of Neurochemistry, vol. 76, pp. 173-181, (2001).
Itsykson, et al., "Derivation of neural precursors from human embryonic stem cells in the presence of noggin", Mol. Cell. Neurosci., vol. 30, pp. 24-36, (2005).
Lindvall, et al., "Grafts of Fetal Dopamine Neurons Survive and Improve Motor Function in Parkinson's Disease", Science, vol. 247, pp. 574-577, (1990).
Nistor, et al., "Human Embryonic Stem Cells Differentiate into Oligodendrocytes in High Purity and Myelinate After Spinal Cord Transplantation", Glia, vol. 49, pp. 385-396, (2005).
Izrael, et al., "Human oligodendrocytes derived from embryonic stem cells: Effect of noggin on phenotypic differentiation in vitro and on myelination in vivo", Mol. Cell. Neurosci., vol. 34, pp. 310-323, (2007).
Li, et al., "Directed Differentiation of Ventral Spinal Progenitors and Motor Neurons from Human Embryonic Stem Cells by Small Molecules", Stem Cells, vol. 26, pp. 886-893, (2008).
Li, et al., "Specification of motoneurons from human embryonic stem cells", Nature Biotechnology, vol. 23, No. 2, pp. 215-221, (2005).
Shin, et al., "Notch signaling regulates neural precursor allocation and binary neuronal fate decisions in zebrafish", Development, vol. 134, pp. 1911-1920, (2007).

(Continued)

*Primary Examiner* — Chris R Tate
*Assistant Examiner* — Douglas F White
(74) *Attorney, Agent, or Firm* — Vorys, Sater, Seymour and Pease LLP; Susanne M. Hopkins; Ari G. Zytcer

(57) ABSTRACT

Provided is a method for directing differentiation of neural progenitors with a caudal and ventral specification into motor neurons including culturing neural progenitors in a culturing medium including a basic medium supplemented by at least one inhibitor of the Notch signaling pathway whereby the neural progenitors differentiate into postmitotic motor neurons. The resulting motor neurons may be used for drug development, as carriers, e.g. for gene therapy of protein delivery as well as for transplantation for the purpose of treating a motor neuron disease.

17 Claims, 9 Drawing Sheets

(56) References Cited

OTHER PUBLICATIONS

Lim, et al., "Derivation of Motor Neurons from three Clonal Human Embryonic Stem Cell Lines", Current Neurovascular Research, vol. 3, pp. 281-288, (2006).

Billon, et al., "Normal timing of oligodendrocyte development from genetically engineered, lineage-selectable mouse ES cells", Journal of Cell Science, vol. 115, No. 18, pp. 3657-3665, (2002).

John, et al., "Multiple sclerosis: Re-expression of a developmental pathway that restricts oligodendrocyte maturation", Nature Medicine, vol. 8, No. 10, pp. 1115-1121, (2002).

Reubinoff, et al., "Neural progenitors from human embryonic stem cells", Nature Biotechnology, vol. 19, pp. 1134-1140, (2001).

Lowell, et al., "Notch Promotes Neural Lineage Entry by Pluripotent Embryonic Stem Cells", PLoS Biology, vol. 4, Issue 5, e121, pp. 0805-0818, (2006).

Wichterle, et al., "Directed Differentiation of Embryonic Stem Cells into Motor Neurons", Cell, vol. 110, pp. 385-397, (2002).

Peschanski, et al., "Rationale for Intrastriatal Grafting of Striatal Neuroblasts in Patients with Huntington's Disease", Neuroscience, vol. 68, No. 2, pp. 273-285, (1995).

Wang, et al., "Notch Receptor Activation Inhibits Oligodendrocyte Differentiation", Neuron, vol. 21, pp. 63-75, (1998).

* cited by examiner

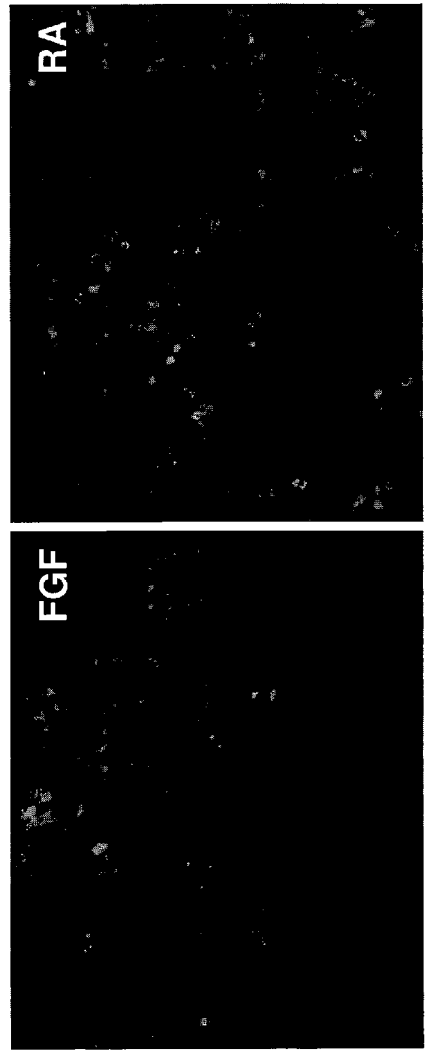
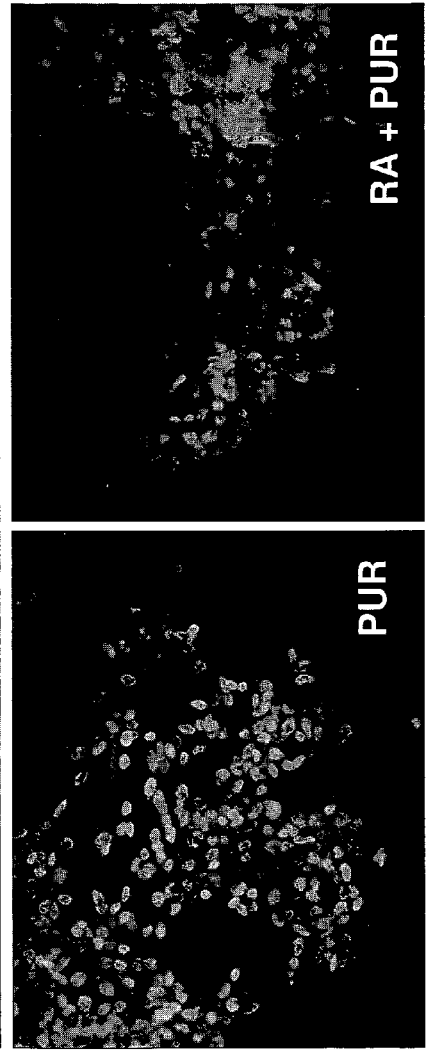

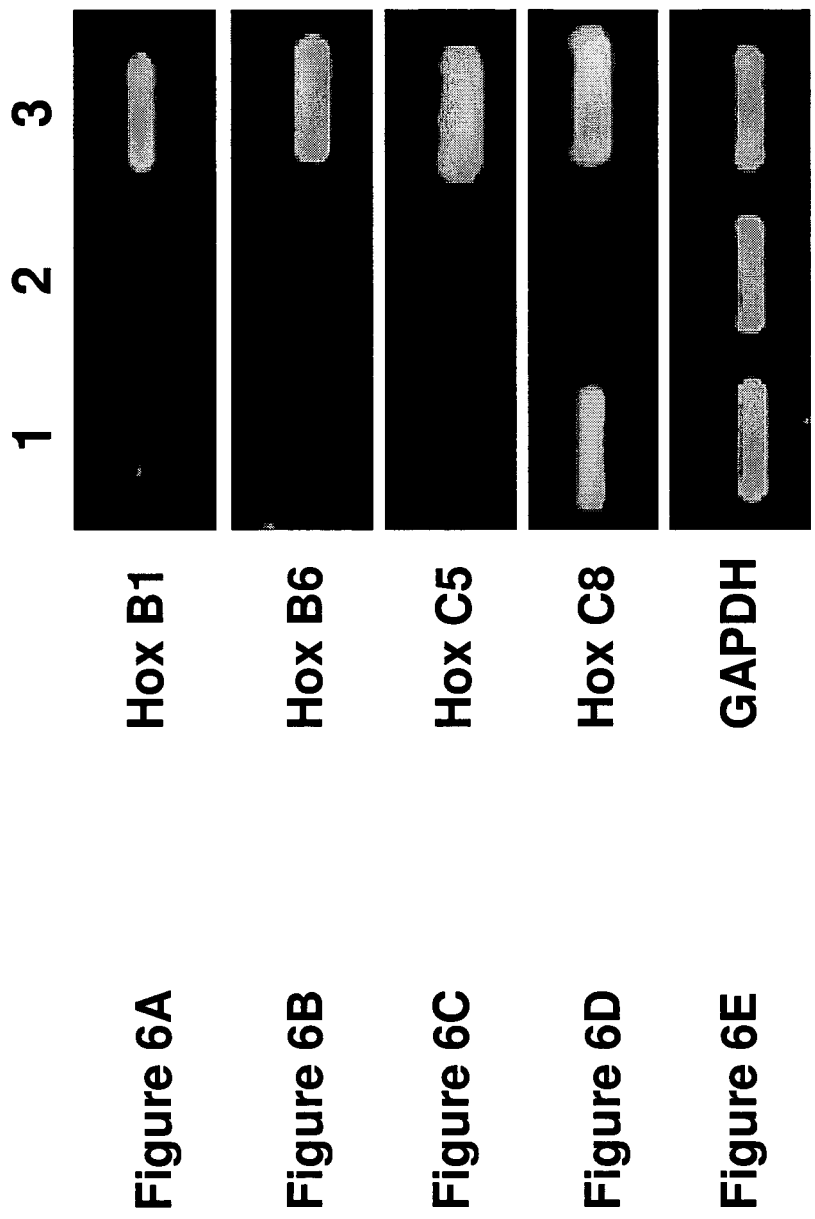

MOTOR NEURONS DEVELOPED FROM STEM CELLS

This is a National Phase Application filed under 35 U.S.C. §371 as a national stage of PCT/IL2009/000367, filed on Apr. 5, 2009, claiming the benefit under 35 U.S.C. §119(e) of U.S. Provisional Application No. 61/064,854, filed on Mar. 31, 2008, the content of each of which is hereby incorporated by reference in its entirety.

FIELD OF THE INVENTION

This invention relates to methods for directing differentiation of stem cells towards neuronal fate.

The Sequence Listing submitted in text format (.txt) on Nov. 15, 2010, named "1916832_$_{ST}$25.txt", (created on Tuesday, Nov. 9, 2010, 2.80 KB), is incorporated herein by reference.

BACKGROUND OF THE INVENTION

Self-renewing, pluripotent human stem cells may provide a virtually unlimited donor source of neural progeny for far reaching applications. Neural differentiation of human pluripotent stem cells may provide access to study all steps of human neurogenesis, and therefore may serve as an in vitro model for the discovery of new genes and the development of new drugs. Neural progeny derived from human pluripotent stem cells may serve for testing and high throughput screening of molecules for neurotoxic, teratogenic, neurotrophic, neuroprotective and neuroregenerative effects. Human pluripotent stem cells may serve as an unlimited source of neural cells for transplantation and gene therapy of neurological disorders [1-3].

Reubinoff et. al. pioneered the development of highly enriched cultures of developmentally competent early neural precursors (NPs) from human embryonic stem cells (hESCs) [4]. In addition, Itsykson et al demonstrated the controlled conversion of hESC into NPs in chemical defined culture conditions, in the presence of the BMP antagonist noggin [5].

The potential involvement of the Notch signaling pathway and the γ-secretase complex in pluripotent cell differentiation has been suggested by several groups. Notch signaling can be modulated by altering the activity of the γ-secretase complex. The proteins which form this complex include Presenilin, nicastrin, aph-1, pen-2 and related proteins[14]. γ-secretase inhibitors were shown to reduce the level of Notch signaling.

Condie et al. [18] describes compositions and methods for the stabilization of pluripotent cells in an undifferentiated state and reduction of percentage of spontaneously differentiated cells in the pluripotent cell culture, by inhibition of components of the γ-secretase complex. On the other hand, incubation of the cells with an activator of Notch signaling resulted in differentiation of the cells into neuronal cells. Condie et al. [18], and also Lowell S. et. al. [12], describe a role for the Notch signaling system in controlling the fate of pluripotent stem cells. Accordingly, activation of Notch signaling in ES cells directs their differentiation towards the neural lineage.

Similarly, also LOWELL et al. [19] disclose that activation of Notch signaling in ES cells promotes differentiation towards a neural fate.

Wang S et al. [15], and Givogri M I et al. [16] discuss the potential role of the Notch system in oligodendroglial differentiation during development. John et al. [17] discuss the potential role of Notch system in controlling remyelination in MS. None of these studies however was performed in humans, or in ES cells, or in ESC-derived neural progenitors. Also, none of these studies concerns spinal cord development.

Differentiation of human embryonic stem cells towards motor neurons (also known as motoneurons) have been previously described [6-8]. However, the efficiency of directing hESC to a motor neuron fate was limited and only 20-50% of the cells in differentiated cultures expressed markers of motor neurons. Differentiation towards a motor neuron fate was mainly induced by two factors. Retinoic acid was used for caudalization and sonic hedgehog (SHH) or its agonist purmorphamine for ventralization.

SUMMARY OF THE INVENTION

The present invention provides highly efficient methods to direct the differentiation of neural precursors towards a motor neuron fate (also known as motoneurons).

It was found that blocking of Notch signaling pathway, e.g. by blocking γ-secretase, augments the differentiation of ventral spinal cord progenitors towards a motor neuron fate. Moreover, inhibition of Notch signaling (e.g. via γ-secretase inhibition) in ES cells results in prevention of differentiation, as previously described [12,18]. In contrast, it has now been found that inhibiting Notch signaling in ES cell-derived neural precursors, as disclosed herein, results in the unexpected opposite effect, namely, in promoting differentiation towards motor neurons.

Thus, there is provided a method for directing differentiation of neural progenitors that have a caudal and ventral specification into motor neurons, the method comprising culturing the neural progenitors in a culturing medium comprising a basic medium supplemented by at least one inhibitor of the Notch signaling pathway whereby said neural progenitors differentiate into postmitotic motor neurons.

Further, the present invention provides a method of directing differentiation of neural precursors into motor neurons comprising:

(a) providing a population of neural precursors;
(b) culturing the neural precursors in a first culturing medium comprising a basic medium supplemented by at least hedgehog (HH) or an HH agonist and with retinoic acid (RA) so as to direct said neural precursors to differentiate into neural progenitors that have a caudal and ventral specification;
(c) culturing the neural progenitors in second culturing medium comprising a basic medium supplemented by at least one inhibitor of the Notch signaling pathway whereby said neural progenitors differentiate into post mitotic motor neurons.

The invention also provides a population of motor neurons differentiated from stem cells obtained by the method of the invention. In one preferred embodiment, the population of motor neurons is used as a model for drug development.

Further provided is the use of a population of motor neurons differentiated from stem cells according to the invention, for the preparation of a medicament.

Finally, the invention provides a package for directing differentiation of neural progenitors that have a caudal and ventral specification into motor neurons, the package comprising a culturing medium comprising a basic medium supplemented by at least one inhibitor of the Notch signaling pathway and instructions for use of the culturing medium for directing differentiation of said neural precursors with caudal and ventral specification into postmitotic motor neurons.

Further provided is a package for directing differentiation of neural precursors into motor neurons comprising
(a) a first culturing medium comprising a basic medium supplemented with at least hedgehog (HH) or an HH agonist and with retinoic acid (RA)
(b) a second culturing medium comprising basic medium supplemented by at least one inhibitor of the Notch signaling pathway;
(d) instructions for use of:
i) the first culturing medium to direct neural precursors into neural progenitors that have a caudal and ventral fate;
iii) the second culturing medium for directing differentiation of said neural progentors with caudal and ventral specification into postmitotic motor neurons.

Finally, there is provided a method for enriching a population of neural progenitors with a caudal and ventral specification, the method comprising incubating said neural progenitors in a culturing medium comprising a basic medium supplemented with N2 serum replacement, a member of dibutyryl cyclic AMP, glial cell derived neurotrophic factors (GDNF), BDNF, and IGF-I.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3A-3D are fluorescent images of immunostaining for Olig-2 after early neural induction followed by 3 weeks of treatment with FGF2 (FIG. 3A), RA (FIG. 3B), Pur (FIG. 3C) and RA+Pur (FIG. 3D).

FIGS. 6A-6E are RT-PCR analyses of the expression of HOX B1 (FIG. 6A), HOX B6 (FIG. 6B), HOX C5 (FIG. 6C) and HOX C8 (FIG. 6D) after early neural induction with FGF2 treatment for 10 days (lane 1) and 17 days (lane 2) as well as early neural induction for 10 days followed by 7 days treatment with RA (lane 3); GAPDH used as a control house keeping gene (FIG. 6E).

DETAILED DESCRIPTION OF THE INVENTION

Figure 1:
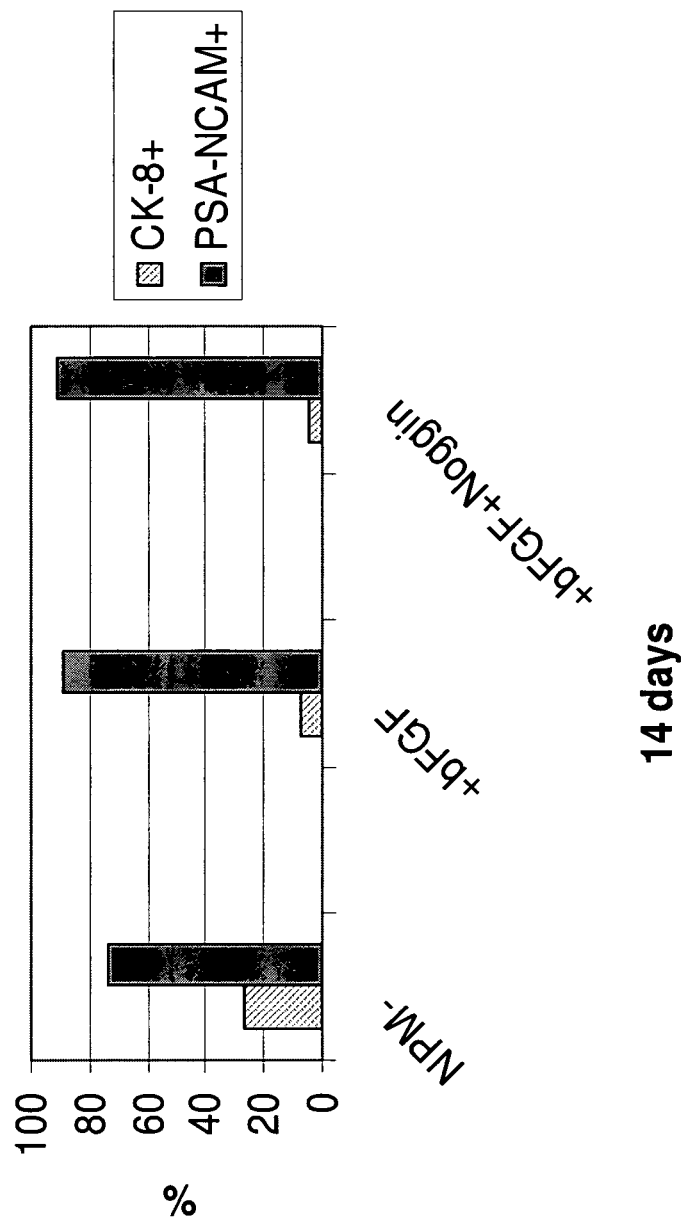
FIG. 1 is a bar graph showing the percentage of cells expressing the early neural marker PSA-NCAM (PSA-NCAM+) and the non-neural epithelial marker cytokeratine 8 (CK+8) from total cell number of cells after early neural induction of hESC clusters, in the presence of FGF2 or FGF2+noggin, as compared to culturing the hESC clusters in the same chemically defined medium (NPM–) without FGFs+noggin.

The present invention is based on the finding that during differentiation of human pluripotent stem cells towards spinal cord derivatives, Notch signaling has a key role in directing differentiation towards motor neurons. Blocking its signaling at an early phase induces the differentiation of spinal cord progenitors towards motor neurons.

Thus, there is provided by the present invention a method for directing differentiation of neural progenitors that have a caudal and ventral specification into motor neurons, the method comprising culturing the neural progenitors in a culturing medium comprising a basic medium supplemented by at least one inhibitor of the Notch signaling pathway whereby said neural progenitors with caudal and ventral specification differentiate into postmitotic motor neurons.

Further, there is provided a method for directing differentiation of neural precursors into motor neurons comprising:
(a) providing a population of neural precursors;
(b) culturing the neural precursors in a first culturing medium comprising a basic medium supplemented by at least hedgehog (HH) or an HH agonist and with retinoic acid (RA) so as to direct said neural precursors to differentiate into neural progenitors that have a caudal and ventral specification;
(c) culturing the neural progenitors in a second culturing medium comprising a basic medium supplemented by at least one inhibitor of the Notch signaling pathway whereby said neural progenitors with caudal and ventral specification differentiate into postmitotic motor neurons.

In one embodiment, the neural precursors are developed from stem cells. As appreciated, the term stem cells refers to cells which under suitable conditions are capable of differentiating into other cell types having a particular, specialized function (i.e., "fully differentiated" cells) while under other suitable conditions are capable of self-renewing and remaining in an undifferentiated state. A "cell" as used herein refers to a single cell as well as to a population of (i.e. more than one) cells. The population may be a pure population comprising a single cell type. Alternatively, the population may comprise more than a single cell type. In one embodiment, the stem cells are pluripotent stem cells, in other embodiments, the stem cells are neural stem cells such as brain derived neural stem cells.

The methods of the invention make use of a population of neural precursors differentiated from stem cells. The neural precursors are uncommitted cells. In this connection, it is noted that the population of neural precursors developed from stem cells are preferably those obtained from human embryonic stem (ES) cells, human induced pluripotent stem cells (iPS cells) or any other "reprogrammed" human cell being capable of differentiating towards a desired fate. In accordance with one embodiment, the preferred stem cells are pluripotent stem cells.

Pluripotent stem cells may be obtained from the embryonic tissue (ES cells) formed after fertilization, parthenogenetic activation or somatic cell nuclear transfer (e.g., blastomer/s from cleavage stage embryo or morula, blastocyst), or embryonic germ (EG) cells obtained from the genital tissue of a fetus any time during gestation, preferably before 10 weeks of gestation, or from postnatal gonads at any age from birth to adulthood or from induced pluripotent stem cells.

Pluripotent stem cells include also multipotential adult progenitor cells (MAPCs), amniotic fluid-derived stem cells (AFS), marrow-isolated adult multilineage inducible cells (MIAMI).

Further, pluripotent cells include epiblast-derived stem cells (EpiSCs) similar to those recently derived from mouse embryos as well as Fibroblast Growth Factor/Activin/Bio cultivated stem cells (FAB-SCs).

Generally, SCs can be obtained using well-known cell-culture methods. For example, hESC can be isolated from human blastocysts, morulas, cleavage stage embryos or blastomeres. Human blastocysts are typically obtained from human preimplantation embryos, from in vitro fertilized (IVF) oocytes, parthenogenetically activated oocytes or following somatic cell nuclear transfer (SCNT). Alternatively, a single cell human embryo can be expanded to the cleavage stage, morula or blastocyst stage. For the isolation of human ES cells from blastocysts, most commonly the zona pellucida is removed from the blastocyst. The whole blastocyts may be used to derive stem cells or alternatively, the inner cell mass (ICM) is isolated by immunosurgery, in which the trophectoderm cells are lysed and removed from the intact ICM by gentle pipetting. The ICM may be isolated by any alternative method including mechanical methods or with the assistance of laser [Turetsky T, et al. *Laser-assisted derivation of human embryonic stem cell lines from IVF embryos after preimplantation genetic diagnosis.* Hum Reprod. 2008 23(1):46-53]. The ICM, blastomeres or whole intact blastocyte are then plated in a tissue culture flask containing the appropriate medium which enables its outgrowth. Following 9 to 15 days, the outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al. [U.S. Pat. No. 5,843,780; Science 282:1145, 1998; Curr. Top. Dev. Biol. 38:133, 1998; Proc. Natl. Acad. Sci. USA 92: 7844, 1995]; as well as Bongso et al. [Hum Reprod 4: 706, 1989]; Gardner et al. [Fertil. Steril. 69:84, 1998]; and Klimanskaya et al. [Nature. 446: 342, 2007].

Commercially available SCs can also be used to produce the neural precursors in accordance with the invention. hESCs can be purchased from the NIH human embryonic stem cells registry. Non-limiting examples of commercially available embryonic stem cell lines are BG01, BG02, BG03, BG04, CY12, CY30, CY92, CY10, TE03 and TE32.

In accordance with one embodiment of the invention, the neural precursors are provided in the form of spheres enriched with said neural precursors. In accordance with one embodiment the neural precursors differentiated from stem cells are in the form of clusters of stem cells (referred to as "spheres" or "neurospheres"). The spheres are the result of neural precursors agglomerating in spherical formations which continues to grow over the duration of the differentiation procedure. In one embodiment, the spheres are highly enriched with neural precursors. The term "spheres (highly) enriched with neural precursors" is used to denote clusters of pluripotent stem cell derived cells comprising at least 35% neural precursors, at time about 60%, 75% or even 90% neural precursors and preferably between about 35% and 100% neural precursors.

The spheres are provided as free floating spheres. "Free floating spheres" as used herein, refers to a culture system in which the majority of the spheres freely float in the culturing medium. In other words, the spheres survive and propagate in the medium without being attached to a solid or semi solid substrate.

Spheres enriched with neural precursors derived from stem cells may be obtained by culturing stem cells, e.g. pluripotent stem cells (i.e. cells that have the ability to form any adult cell) in a culturing medium that directs differentiation of the stem cells into uncommitted neural precursors. This may include a culturing medium comprising at minimum a basic medium (a cell culture medium usually comprising a defined base solution, which includes salts, sugars and amino acids) supplemented by FGF2 and/or noggin, as described, for example by Itsykson, P., et al.[14]. In this connection, it is noted that noggin, a bone morphgenic protein (BMP) antagonist, is known to prevent the extraembryonic background differentiation of hESCs into non-neural lineage, favoring the differentiation to a neural fate. Alternative BMP antagonists may include chrodin or gremlin. The basic medium may be supplemented only by FGF2, by inhibitors of the TGF-beta pathway, or by any combination of the above factors.

As appreciated by those versed in the art, neural precursors may also be obtained by culturing embryonic stem cells in a chemically defined medium without any factors, or they may be derived in monolayer cultures in chemically defined medium that may be further supplemented with noggin, FGF2, inhibitors of the TGF-beta pathway, or with a combination of these factors.

In the context of the present invention a "culturing medium" includes a combination of elements, at minimum including a basic medium and a serum replacement supplement. The basic medium may be any basic medium known in the art for culturing cells, in particular, for culturing stem cells. In some preferred embodiments, the basic medium is basal, such as Neurobasal™ medium, available from Invitrogen and known to be suitable for culturing neural cells. Alternatively, the basic medium may be DMEM/F-12 also available from Invitrogen.

The culturing medium may further comprise other elements such as, without being limited thereto, an extracellular matrix (ECM) component, particularly for inducing neural precursors from stem cells in flat cultures, additional serum or serum replacements, a culture (nutrient) medium and other exogenously added factors, which together provide suitable conditions that support cell growth. The culturing medium may also be supplemented by an antibacterial agent. The antibacterial agent may be selected from, without being limited thereto, penicillin and/or streptomycin. Further, the culturing medium may be supplemented by non-essential amino acids (NEAA). In the context of the present invention, the term "culture system" will be used to denote cells maintained in a culturing medium.

The term "maintenance" means continuous survival of a cell or population of cells, at times, with an increase in numbers of cells. The continuous survival refers to a survival of the cells for at least 6 weeks, preferably for at least 10 weeks. Further, "proliferation", "propagation", "expansion" and "growth", which may be used interchangeably with each other, refer to such an increase in cell number.

Thus, in the context of the present invention the term "neural precursors developed (or differentiated, or derived) from stem cells" denote the result of non-terminal differentiation of stem cells towards neural fate, the cells being characterized by the expression of at least the cellular markers Pax6 and nestin.

In accordance with the invention, the neural precursors developed from stem cells are subject to a first culturing stage, including culturing in a medium supplemented with at least hedgehog (HH) or an HH agonist and with retinoic acid (RA), two potent enhancers of neuronal differentiation, so as to direct said neural precursors to acquire a caudal and ventral specification.

In one embodiment, the HH is Sonic HH (SHH) agonist selected from purmorphamine (Pur), Hh-Ag1.3 (Curis Company).

A typical concentration range for the HH or HH agonist used in the first culturing stage of the invention is between 0.5 μM and 2.0 μM preferably 0.5 μM; and a typical concentration range for the RA in the first culturing stage of the invention is between 0.5 μM to 20 μM, preferably about 1 μM. Such conditions allow the neural precursors to acquire a caudal and ventral specification and to propagate.

The first culturing stage is conducted for between several days to several weeks, typically, between 1 to 3 weeks.

As indicated above, the first culturing stage results in a culture system comprising a cell population of enriched with neural progenitors having a caudal and ventral specification. The term "neural progenitors having a caudal and ventral specification" as used herein denotes a population of such cells where at least 30%, preferably 70% and more preferably above 90% of the cells exhibit at least one characteristic of neural progenitors having a caudal and ventral fate. Such characteristics include, without being limited thereto the expression by cells having a caudal and ventral specification/fate of one or more of the following cell markers: Olig2, HoxB1, HoxB6, HoxC5, and HoxC8.

In the context of the present invention a "cell marker" refers to is any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the cell type of interest. The markers can also be identified by a biochemical or enzyme assay that depends on the function of the gene product. Associated with each marker is the gene that encodes the transcript, and the events that lead to marker expression. A marker is said to be preferentially expressed in an undifferentiated or differentiated cell population, if it is expressed at a level that is at least 5 times higher (in terms of total gene product measured in an antibody or PCR assay) or 5 times more frequently (in terms of positive cells in the population). Markers that are expressed 10, 100, or 10,000 times higher or more frequently are increasingly more preferred.

In accordance with the method of the invention, the neural progenitors that have a caudal and ventral specification are then subjected to conditions that direct their further differentiation into functional postmitotic motor neurons. Such conditions comprise a second culturing stage making use of a second culturing medium comprising at least one inhibitor of the Notch signaling pathway. The at least one inhibitor of the Notch signaling pathway used in the second culturing stage may be any inhibitor of any component participating in the pathway. The component may be a small molecular weight compound as well as a polymer. In one embodiment, the component is an amino acid molecule (protein, peptide, or polypeptide) or nucleic acid encoding the amino acid sequence participating in the pathway.

In a further embodiment, the amino acid molecule or nucleic acid encoding same and that is involved in the Notch signaling pathway belongs to the γ-secretase complex. Non-limiting examples of γ-secretase complex inhibitors include non-transition stage analogues such as the highly specific γ-secretase complex, N-(3,5-Difluorophenacetyl)-L-alanyl]-S-phenylglycine t-butyl ester DAPT [Dovey et al., [13]] compound E transition state analogues, helical peptides containing α-aminoisobutyric acid (Aib), Fenchylamine Sulfonamide compounds, NSAIDs, and benzodiazepines.

Culturing with an inhibitor of the Notch signaling pathway comprises incubation for about 7 to 14 days. In accordance with one embodiment, the inhibitor is added to the cells after these were plated.

As a result of culturing with the Notch signaling pathway a culture system comprising at least about 20%, preferably between about 40% to about 60%, most preferably above 60% of postmitotic motor neurons are obtained, as evidenced by the expression of HB9 protein.

At times, to achieve effective differentiation into motor neurons, it is preferable that the neural progenitors having a caudal and ventral fate be propagated in a chemically defined medium for several weeks, prior to subjecting the neural precursors to the said at least one inhibitor of the Notch signaling pathway. The propagation stage may be for about 2 to about 20 weeks, preferably for about 4 to 6 weeks.

The chemically defined medium for propagation may comprises the basic media (e.g. Neurobasal™) supplemented with serum replacement such as N2, any member one of dibutyryl cyclic AMP (dbcAMP), glial cell derived neurotrophic factors (GDNF) and the neutrophins, such as BDNF, as well as growth factors, such as IGF-I.

In accordance with one particular embodiment, the chemically defined medium is Neurobasal™ medium supplemented by 1% non-essential amino-acids, 1% N2 or 0.5% N2 combined with 1% B27, 0.5 μM-1 μM, preferably 1 μM, db-cAMP and between about 5 ng/ml and about 30 ng/ml, preferably about 10 ng/ml, of BDNF, GDNF and IGF-I.

The cells may be propagated for a long period of time before being subjected to the postmitotic differentiation, i.e. to the second culturing stage. A long period of time includes from several weeks to several months during which the spheres are cultured in suspension, as free floating spheres.

The method disclosed herein may comprise one or more steps of culturing medium refreshment (i.e. the replacement of at least 50% of the culturing medium). It is appreciated that by said medium refreshment, dead cells and their fragments are gradually removed. Culturing medium may be refreshed at least every 2-3 days and most preferably at least every 2 days. The medium refreshment may include the replacement of a portion of the basic media only, as well as the replacement of a portion of the basic media including one or more of its components as described herein. Further, it is appreciated that the methods may comprise different media replacements, e.g. at times only the replacement of the basic medium, and at other time points, the replacement of the basic medium comprising one or more of the supplements.

The motor neurons obtained by the method of the present invention may have a variety of applications.

In accordance with one embodiment, the motor neurons can be used in cellular models of human motor neuron disease, where such models could be used for basic research and drug discovery, e.g., to find treatments for motor neuron diseases or disorders including but not limited to: amyotrophic lateral sclerosis (ALS), also called Lou Gehrig's disease or classical motor neuron disease; progressive bulbar palsy, also called progressive bulbar atrophy; pseudobulbar palsy; primary lateral sclerosis (PLS); progressive muscular atrophy; spinal muscular atrophy (SMA, including SMA type I, also called Werdnig-Hoffmann disease, SMA type II, and SMA type III, also called Kugelberg-Welander disease); Fazio-Londe disease; Kennedy disease, also known as progressive spinobulbar muscular atrophy; congenital SMA with arthrogryposis; or post-polio syndrome (PPS).

In an exemplary embodiment, somatic cell nuclear transfer can be used to insert DNA from a patient with a genetic defect or a defect of unknown origin in their motor neurons, into an oocyte, followed by the isolation of a human embryonic stem cell line, followed by the differentiation of that line into a population of motor neurons. The thus formed population may then be used as a cellular model for the disorder associated with the genetic defect or any other abnormality carried by these cells. The cellular model may be used for the development of drugs. In addition, the thus formed population may serve for drug development and testing for the specific patient from which they were developed in the course of personalized medicine.

In an other exemplary embodiment stem cell, neural precursors or neural progenitors may be developed from the gonads, bone marrow, brain biopsy or any "reprogrammed" cells of patients with motor neuron disorder of any etiology, and directed to differentiate into a population of motor neurons. The thus formed population may then be used as a cellular model for the motor neuron disorder of the patient. The cellular model may be used for the development of drugs. In addition, the thus formed population may serve for drug development and testing for the specific patient from which they were developed in the course of personalized medicine.

The motor neurons may serve for testing and high throughput screening of molecules for neurotoxic, teratogenic, neurotrophic, neuroprotective and neuroregenerative effects.

In accordance with another embodiment, the motor neurons can be used for studying exogenous diseases and disorders of motor neurons. In one exemplary embodiment, the cells can be used to study viral infections of motor neurons such as polio.

In yet another embodiment, the motor neurons can be used for transplantation into any tissue of interest, where such tissues could be neural tissues (central nervous system or peripheral nervous system, e.g. spinal cord, nerve bundles, motor nerves, nerve ganglia) or non-neural tissues (muscle, liver, lungs). The motor neurons can be transplanted into the spinal cord at any position from the cervical to lumbar regions. One of skill in the art can determine what procedures would be necessary for transplanting the cells into a particular position in the spinal cord, e.g., in some embodiments, a laminectomy may be appropriate to facility entry to the spinal cord, while in other embodiments the cells could be administered by directly accessing the spinal cord, as may be possible for neonatal applications, or administration to adult subjects by inserted the injection apparatus between vertebral bodies (similar to a spinal tap), to deliver the cells either into nervous tissue or intra thecal or into any other appropriate site.

In accordance with one aspect of the invention, when the motor neurons are used in a therapeutic application wherein the cells are expected to exhibit functions similar or identical to motor neuron functions. In one embodiment, the cells are transplanted using procedures to target the cells to selected sites. In an exemplary embodiment, when cells are introduced into the spinal cord, the cells may be targeted to spinal cord grey matter, including the dorsal or ventral horn of the grey matter. In another exemplary embodiment, cells can be targeted to other sites including, but not limited to, an emerging ventral or dorsal root, a dorsal root ganglion, a spinal nerve, a peripheral nerve a motor nerve, or any other appropriate site as determined by one of skill in the art. In one preferred embodiment, the cells are transplanted directly or indirectly (e.g. ex vivo) to mammals, preferably, to humans.

In some other embodiments, the motor neurons may be used as carriers for gene therapy, or as carriers for protein delivery.

The invention also provide a package for directing differentiation of neural progenitors that have a caudal and ventral specification into motor neurons comprising culturing medium comprising a basic medium supplemented by at least one inhibitor of the Notch signaling pathway and instructions for use of the culturing medium for directing differentiation of said neural progenitors with caudal and ventral specification into postmitotic motor neurons.

The invention also provides a package for directing differentiation of neural precursors differentiated from stem cells into motor neurons comprising:
(a) a first culturing medium comprising a basic medium supplemented with at least hedgehog (HH) or an HH agonist and with retinoic acid (RA);
(b) a second culturing medium comprising a basic medium supplemented by at least one inhibitor of the Notch signaling pathway;
(d) instructions for use of:
   i) the first culturing medium to direct neural precursors differentiated from stem cells to differentiate into neural progenitors that have a caudal and ventral specification;
   iii) the second culturing medium for directing differentiation of said neural progenitors with caudal and ventral specification into postmitotic motor neurons.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

As used in the specification and claims, the forms "a", "an" and "the" include singular as well as plural references unless the context clearly dictates otherwise. For example, the term "a stem cell" includes one or more stem cells, and the term "stein cells" includes one stem cell as well as more than one stem cell.

As used herein, the term "or" means one or a combination of two or more of the listed choices.

Further, as used herein, the term "comprising" is intended to mean that the methods includes the recited elements, but does not exclude others. Similarly, "consisting essentially of" is used to define methods that include the recited elements but exclude other elements that may have an essential significance on the characteristics of the cell populations obtained by the methods of the invention. For example, a method making use of a culture medium consisting essentially of a basic medium and medium supplements will not include or will include only insignificant amounts (amounts that will have an insignificant effect on the characteristics of the resulting cells i) of other substances that have an effect on fate of the original cells. Also, a method making use of a culture medium consisting essentially of the elements as defined herein would not exclude trace contaminants. "Consisting of" shall mean excluding more than trace amounts of other elements. Embodiments defined by each of these transition terms are within the scope of this invention.

Further, all numerical values, e.g., concentration or dose or ranges thereof, are approximations which are varied (+) or (−) by up to 20%, at times by up to 10%, from the stated values. It is to be understood, even if not always explicitly stated that all numerical designations are preceded by the term "about". It also is to be understood, although not always explicitly stated, that the reagents described herein are merely exemplary and that equivalents of such are known in the art.

It is appreciated that certain features disclosed herein, which are, for clarity, described in the context of separate embodiments, may also be provided in combination in a single embodiment. Conversely, various features of the present disclosure, which are, for brevity, described in the context of a single embodiment, may also be provided separately or in any suitable sub-combination.

Although the present disclosure has been described in conjunction with specific embodiments thereof, it is evident that many alternatives, modifications and variations will be apparent to those skilled in the art.

All publications, patents and patent applications mentioned in this specification are herein incorporated in their entirety by reference into the specification.

The invention will now be described with reference to the following non-limiting examples.

DETAILED DESCRIPTION OF NON-LIMITING EMBODIMENTS

Methods
hESC Culture

Undifferentiated hESCs were routinely propagated on mitotically inactivated human foreskin fibroblasts in 85% Knockout (KO) DMEM medium supplemented with 15% Knockout Serum replacement (KO-SR), 2 Mm, 1-glutamine, 1% nonessential amino acids, 50 U/ml penicillin, 50 µg/ml, streptomycin (all from Invitrogen) and basic fibroblast growth factor (rh-FGF2; 4 ng/ml, (Peprotech).

The hESCs were passaged enzymatically with collagenase IV 1 mg/ml (Invitrogen) every 7 days.
Induction of hESCs to Differentiate into Neural Precursors To develop spheres enriched for neural precursors, hESC colonies were removed intact from the feeders, 6 days after passage, with collagenase IV. They were cultured in low adherent culture dishes (HydroCell) in DMEM/F12 (1:1) basal medium (Invitrogen), supplemented with 2% B27, 2 mM glutamine, 50 units/ml penicillin, 50 µg/ml streptomycin (all from Invitrogen), and 20 ng/ml rh-FGF-2 (Peprotech). In some experiments the medium was also supplemented with noggin 600-700 ng/ml (both from R&D) for 14-16 days.

The medium was refreshed twice a week.
Derivation of Motor Neurons

The neural precursors highly enriched spheres were transferred to the same basal medium as above supplemented with 2 mM L-glutamine (Invitrogen), 50 units/ml penicillin (Invitrogen), 50 µg/ml streptomycin (Invitrogen), 1% non-essential amino-acids (Invitrogen) and 1% N2 (Invitrogen). The medium was further supplemented with 1 µM retinoic acid ("RA"; Sigma) or 0.5 µM purmorphamine ("Pur"; a hedgehog agonist; Merck), or combination of Pur and RA, for 3 weeks.

Alternatively, the spheres were cultured in the same medium supplemented with 1 µM RA (Sigma) for 1 week. Followed by further culturing the spheres in neurobasal medium (Invitrogen) supplemented with 2 mM L-glutamine (Invitrogen), 50 units/ml penicillin (Invitrogen), 50 µg/ml streptomycin (Invitrogen), 1% non-essential amino-acids (Invitrogen), N2 (Invitrogen), 1 µM db-cAMP (Sigma) and 1 µM RA (Sigma), or 0.5 µM Pur (Merck), or combination of RA and Pur, for 2-3 weeks.

The spheres were then further cultured in the same neurobasal medium supplemented with 2 mM L-glutamine, 50 units/ml penicillin, 50 µg/ml streptomycin, 1% non-essential amino-acids, 1% N2 (all from Invitrogen), 1 µM db-cAMP and 10 ng/ml of BDNF, GDNF and IGF-I (all from Peprotech). This medium was designated as motor neuron medium (MNM). The clusters could be cultured in suspension in this medium for prolonged periods (5 months). At various time points along this period the cells were plated on 10 µg/ml Poly-D-Lysine (Sigma) and 5 µg/ml laminin (Sigma) for terminal differentiation in the presence or absence of the γ-secretase inhibitor [N-(3,5-Difluorophenacetyl)-L-alanyl]-S-phenylglycine t-butyl ester (DAPT; 1 µM, Sigma).
Immunofluorescent Staining:

The following primary antibodies were used: polyclonal rabbit anti Isl1 (1:750, Abcam), mouse anti HB9 (1:50, DSHB), polyclonal goat anti CHAT (1:200, R&D), and goat anti olig2 (1:75, R&D).

The following secondary antibodies: goat anti-rabbit conjugated to Cy-3 (1:1000, Jackson), goat anti-mouse conjugated to Cy-3 (1:500, Jackson), donkey anti goat conjugated to rhodamin (1:300, Jackson), Texas red or Alexa 488-conjugated goat anti-mouse IgM (1:100, Jackson), goat anti-rabbit IgG (1:100, Molecular Probes), goat anti-mouse IgG (1:100, Molecular Probes) or donkey anti-goat IgG (1:250, Jackson) were used as secondary antibodies, where appropriate.
RT-PCR Total RNA was extracted from free-floating clusters after 2 and 3 weeks of treatment with RA, Pur or both. Total RNA was isolated using TRI-reagent (Sigma) followed by treatment with RNase-free DNase (Ambion). cDNA synthesis was carried out using Moloney murine leukemia virus (M-MLV) reverse transcriptase and random primers, according to the manufacturers' instructions (Promega). To analyze relative expression of different mRNAs, the amount of cDNA was normalized based on the signal from GAPDH mRNA. PCR was carried out using standard protocols with Taq DNA Polymerase (Promega). Amplification conditions were as follows: denaturation at 94° C. for 30 seconds, annealing at 55° C. for 30 seconds, and extension at 72° C. for 45 seconds. The number of cycles varied between 30 and 40, depending on particular mRNA abundance. Primer sequences (forward and reverse 5'-3') were as shown in Table 1 (sequence identification number (SEQ ID NO.) according to the Sequence Listing is also provided):

TABLE 1

Primer sequences

| Gene | Forward primer | SEQ ID NO. | Reverse Primer | SEQ ID NO. |
|---|---|---|---|---|
| HoxB1 | TCAGAAGGAGACGGAGGCTA | 1 | AGCTGCCTTGTGGTGAAGTT | 2 |
| HoxB6 | AAGTGCTCCACTCCGGTCTA | 3 | GCTGAGCAGTTTGCTCTCCT | 4 |
| HoxC5 | GACGGGTTAGACAGCCAAAG | 5 | GCCTCTAGGACCACTTGCTG | 6 |
| HoxC8 | CTCAGGCTACCAGCAGAACC | 7 | CTTCAATCCGACGTTTTCGT | 8 |
| Olig-2 | GCTGTGGAAACAGTTTGGGT | 9 | AAGGGTGTTACACGGCAGAC | 10 |
| HB9 | CAAGAAACAGCGAGAGGGAG | 11 | AACGCTCGTGACATAATCCC | 12 |
| NGN2 | TAGAGCTGCCATTTCTGCTACCCA | 13 | CGCCACCCTTGGCTTTGACAATAA | 14 |
| Isl-1 | CTGTGCTGAACGAGAAGCAG | 15 | TTTCCAAGGTGGCTGGTAAC | 16 |
| GAPDH | AGCCACATCGCTCAGACACC | 17 | GTACTCAGCGCCAGCATCG | 18 |

Results

To induce the differentiation of hESCs towards motor neurons, hESC clusters were initially cultured in chemically defined medium supplemented with FGF2 with or without noggin for two weeks. At the end of this culture period the clusters acquired round morphology typical of neural spheres. Analysis of the phenotype of the cells within the clusters demonstrated that they were highly enriched for neural precursor cells expressing PSA-NCAM (FIG. 1).

Figures 2A, 2B, 2C, 2D:
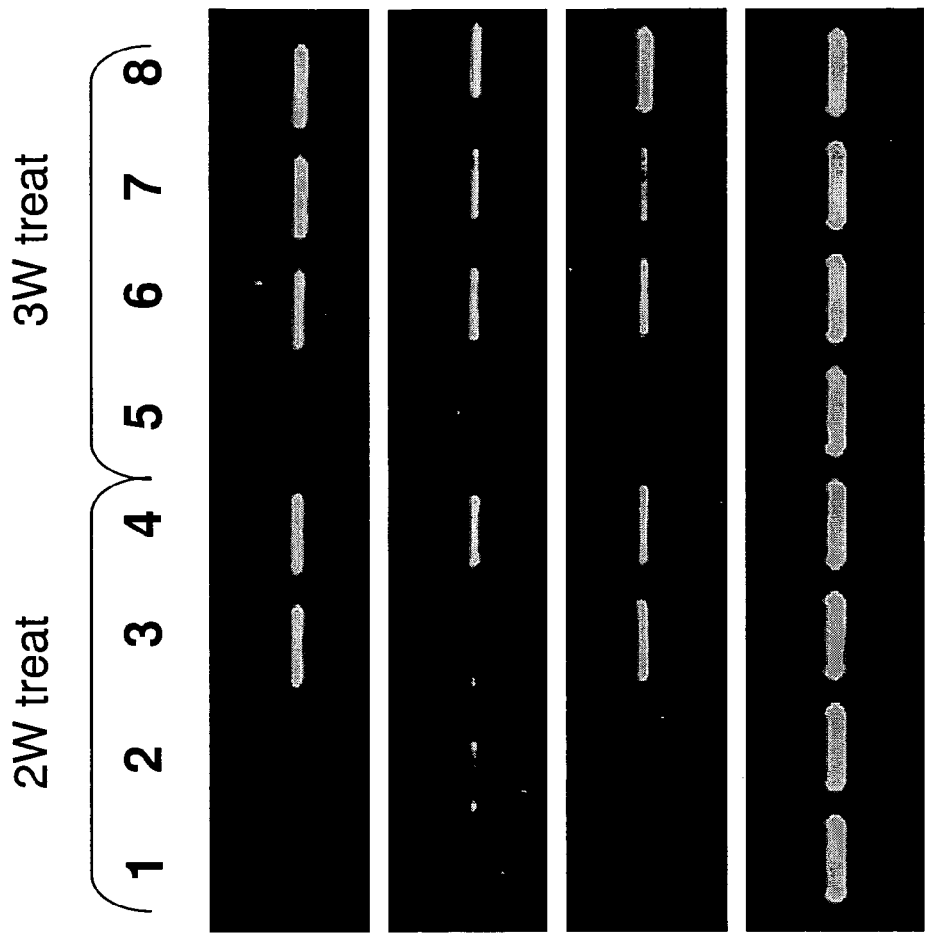
FIGS. 2A-2D are RT-PCR analyses of the expression of transcripts of Olig2 (FIG. 2A), Ngn2 (FIG. 2B), and HB9 (FIG. 2C) after 2 weeks of early neural induction followed by 2 weeks (2 W) or 3 weeks (3 W) of treatment with either FGF2 (lanes 1 and 5), retinoic acid (RA, lanes 2 and 6), purmorphamine (Pur, lanes 3 and 7) and RA and Pur (lanes 4 and 8). GAPDH used as a control house keeping gene (FIG. 2D).

Following this initial induction of early neural differentiation, the role of purmorphamine (Pur) and retinoic acid (RA) in further specification towards a caudal and ventral fate was examined. The neural precursors were further cultured 2-3 weeks with Pur, RA, or the combination of RA & Pur as well as with FGF2 as a control. Caudalization and ventralization were studied by analyzing the expression of Olig-2, Ngn2 and HB9 transcripts (FIGS. 2A, 2B and 2C). When treatment with Pur or RA was compared after 2 weeks (lanes 2 and 3), Pur induced the expression of Olig-2 and HB9 transcripts while RA did not, suggesting that Hedgehog signaling has a role in inducing the expression of these key transcription factors. After 3 weeks of treatment both Pur and RA induced the expression of Olig-2 and HB9 (lanes 6 and 7 in FIGS. 2A and 2C). Without being bound by theory, induction of expression of these transcription factors by RA after 3 weeks (lane 6 in FIGS. 2A and 2C) may be related to RA-mediated induction of endogenous SHH gene expression. Treatment with both Pur and RA induced the expression of Olig-2, HB9 and Ngn2 after 2 and 3 weeks (lanes 4 and 8 in FIGS. 2A, 2B and 2C). Treatment with FGF2 in control experiments did not induce the expression of either genes after 2 or 3 weeks (lanes 1 and 5 in FIGS. 2A, 2B and 2C).

Figure 4B:
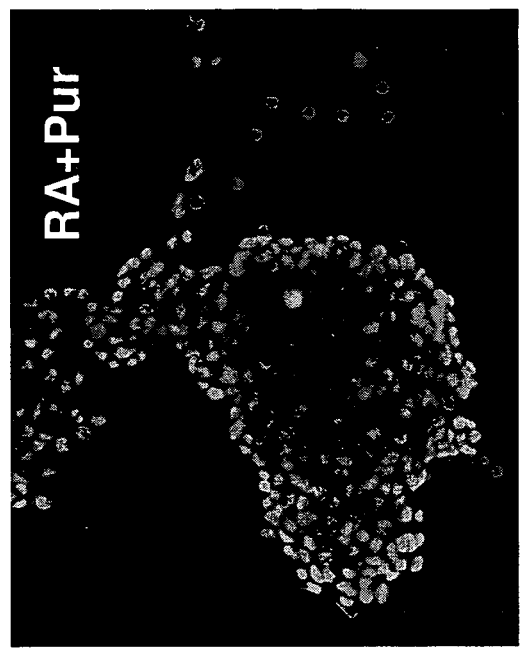
FIGS. 4A-4B are fluorescent images of immunostaining for Isl-1 after early neural induction followed by 3 weeks of treatment with FGF2 (FIG. 4A) and RA+Pur (FIG. 4B).
Figure 4A:

The above findings were confirmed by immunostaining (FIG. 3A-3D). Treatment with FGF2 or RA for 3 weeks did not induce the expression of Olig-2 (FIG. 3A and FIG. 3B), while Pur and the combination of Pur and RA induced the expression of Olig-2 (FIG. 3C and FIG. 3D) in 24-54% of the cells. Isl-1 which was not expressed in the FGF2-treated control cell population (FIG. 4A), was expressed by the majority (60-79%) of the cells after treatment with RA+Pur (FIG. 4B).

Figure 5A:
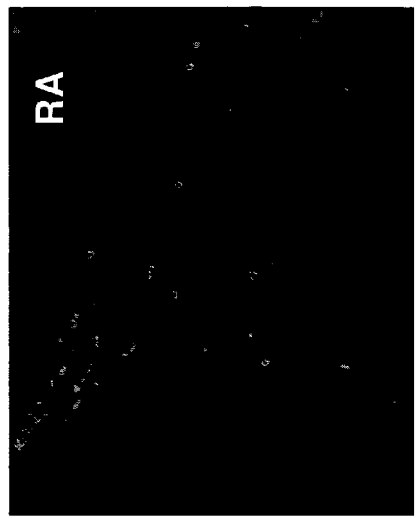
FIGS. 5A-5D are fluorescent images of immunostaining for HB9 after 6 weeks propagation and maturation in a medium supporting motor neurons (MNM) that followed early neural induction, 1 week of RA treatment and 3 weeks treatment with FGF2 (FIG. 5A), RA (FIG. 5C), Pur (FIG. 5C) and RA+Pur (FIG. 5D).
Figure 5B:
Figure 5C:
Figure 5D:
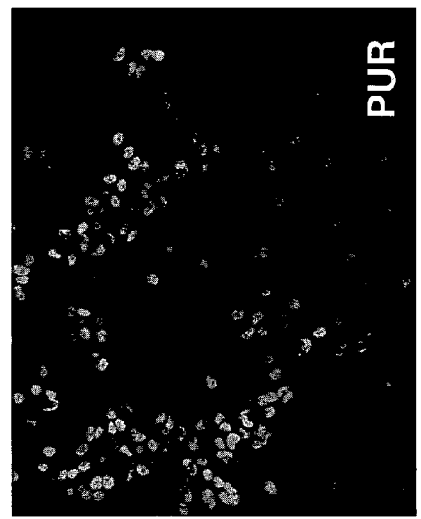

Given these results that indicated the role of RA and Pur in inducing caudal and ventral fate, further studies were perform as follows; the neural precursors were treated with RA for 1 week, which was then followed by 3 weeks treatment with Pur or RA+Pur. Control cell populations were treated during the three weeks period with RA or FGF2 only. After further maturation of the spheres for 4-6 weeks in MNM, further evidence for the ventral specification was demonstrated by the expression of HB9 protein in up to 66% of the cells. HB9 was not expressed after maturation that followed the 3 weeks treatment with FGF2 or RA (FIG. 5A or FIG. 5B, respectively). Its expression was induced after maturation that followed 3 weeks treatment with Pur (66% of total cells; FIG. 5C) or RA+Pur (32% of total cells; FIG. 5D).

Figure 7B:
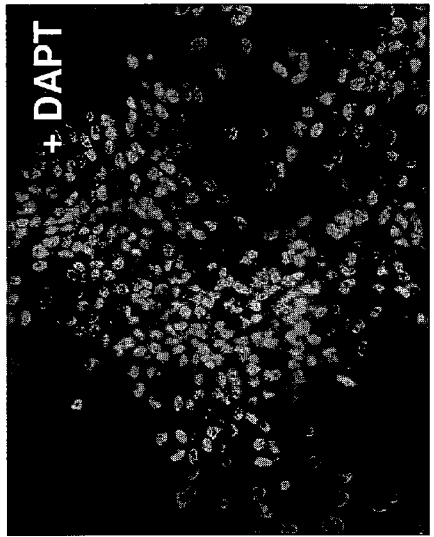
FIGS. 7A-7D are fluorescent images of immunostaining for HB9 after the following treatments: 2 weeks early neural induction, 1 week of RA treatment, 3 weeks Pur (FIG. 7A) or Pur+RA (FIG. 7C) treatment followed by 4 weeks maturation in MNM; the cells were plated during the last week of maturation and DAPT was added during the last week of maturation in cultures that were induced with Pur (FIG. 7B) or Pur+RA (FIG. 7D).
Figure 7D:
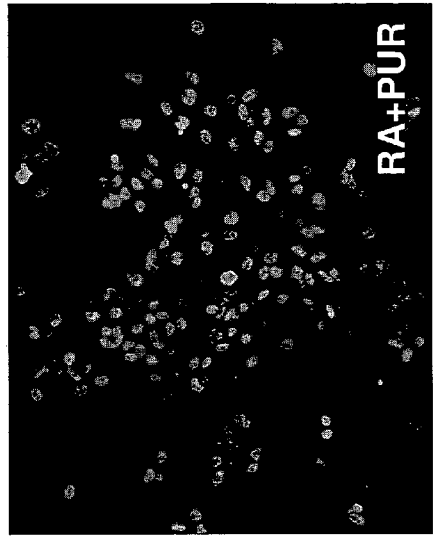
Figure 7A:
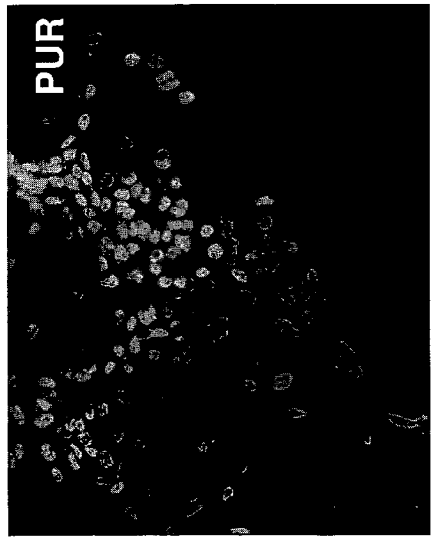
Figure 7C:
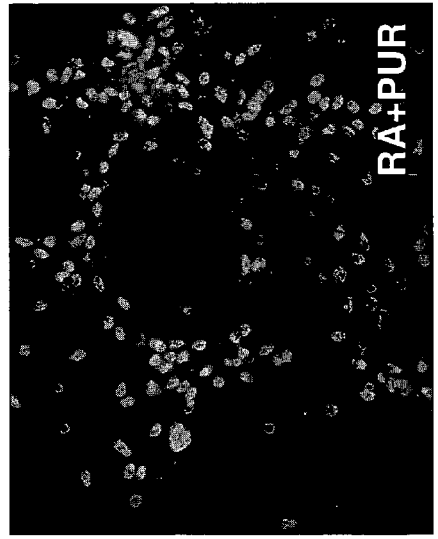
Figure 8A:
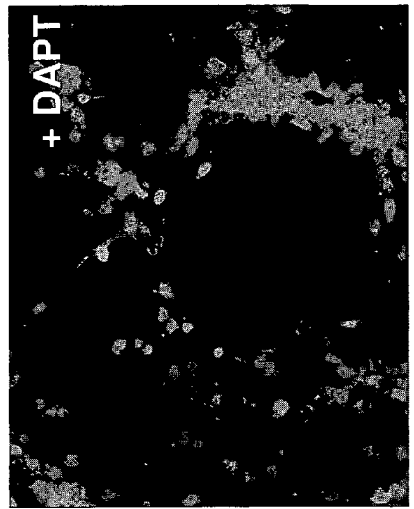
FIGS. 8A-8D show fluorescent images of immunostaining for CHAT after the following treatments: 2 weeks early neural induction, 1 week of RA treatment, 3 weeks Pur (FIG. 8A) or Pur+RA (FIG. 8C) followed by 4 weeks maturation in MNM; the cells were plated during the last week of maturation and DAPT was added during the last week of maturation in cultures that were induced with Pur (FIG. 8B) or Pur+RA (FIG. 8D).
Figure 8B:
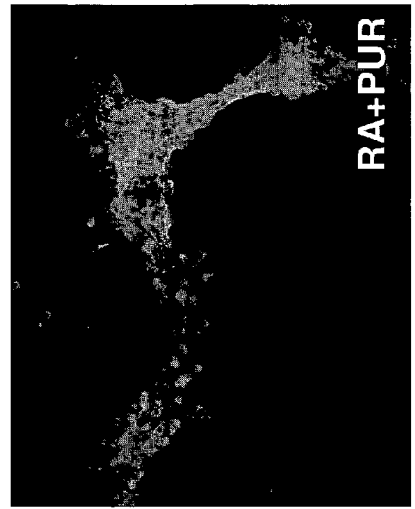
Figure 8C:
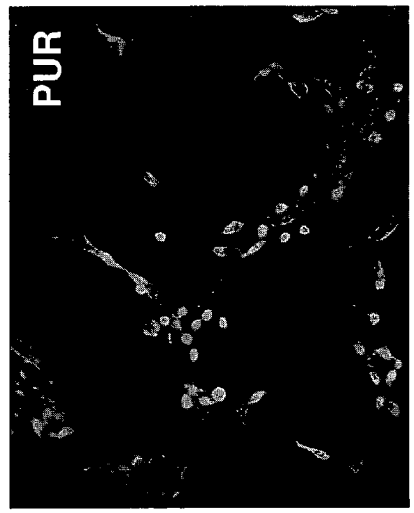

In a similar set of experiments, after initial early neural induction in the presence of FGF2, the spheres were induced to take a caudal fate by 7 days treatment with RA. RA treatment induced the expression of HOX B1 (FIG. 6A), HOX B6 (FIG. 6B), HOX C5 (FIG. 6C) and HOX C8 (FIG. 6D), which are expressed during caudalization of the neural tube (induction with FGF2 treatment for 10 days (lane 1) and 17 days (lane 2) as well as early neural induction for 10 days followed by 7 days treatment with RA (lane 3)). This was further followed by ventralization which was induced by Pur in the presence or absence of RA for 2-3 weeks. At this stage Olig-2, which is expressed by neural progenitors in the pMN domain of the ventral neural tube, was expressed by 23-54% of the cells within the spheres. The spheres were further allowed to mature in MNM for 2-6 weeks followed by plating on laminin and terminal differentiation in the same medium. After 4 weeks of maturation, 20-50% of the cells expressed HB9 (FIGS. 7A and 7C) as well as CHAT (FIGS. 8A and 8C)

Figure 8D:
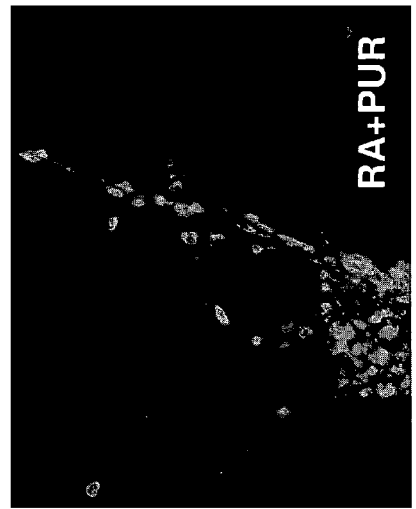
Figure 9:
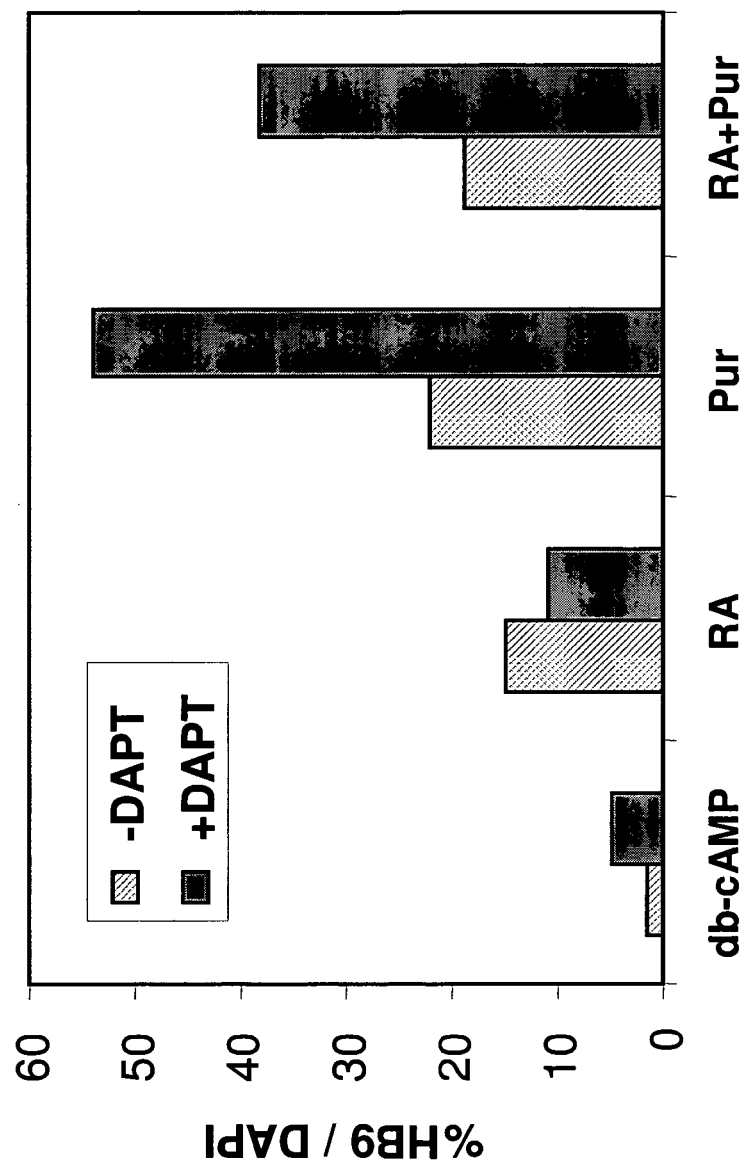
FIG. 9 is a graph showing the percentage of HB9 expressing cells from total cell number after the following treatments: 2 weeks early neural induction, 1 week of RA treatment, 3 weeks db-cAMP, RA, Pur and Pur+RA followed by 4 weeks maturation in MNM; with and without the cells being plated during the last week of maturation in the presence or absence of DAPT (+DAPT and –DAPT, respectively).

To further enhance the motor neuron differentiation, caudalization and ventralization were followed by blocking Notch signaling with the γ-secretase inhibitor DAPT. After 2-3 weeks of maturation in MNM, the spheres were plated on laminin and terminally differentiated in the presence of DAPT for 7-10 days. The percentage of HB9+ cells was increased by 1.5-2 folds to 40-70% of total cells in the presence of DAPT (FIGS. 7B, 7D and 9) DAPT treatment significantly augmented the neurite outgrowth and branching from CHAT expressing cells (FIGS. 8B and 8D).

References

1. Lindvall, O., Brundin, P., Widner, H., Rehncrona, S., Gustavii, B., Frackowiak, R., Leenders, K. L., Sawle, G., Rothwell, J. C., Marsden, C. D., et al. 1990. Grafts of fetal dopamine neurons survive and improve motor function in Parkinson's disease. *Science* 247:574-577.
2. Peschanski, M., Cesaro, P., and Hantraye, P. 1995. Rationale for intrastriatal grafting of striatal neuroblasts in patients with Huntington's disease. *Neuroscience* 68:273-285.
3. Snyder, B. J., and Olanow, C. W. 2005. Stem cell treatment for Parkinson's disease: an update for 2005. *Curr Opin Neurol* 18:376-385.
4. Reubinoff, B. E., Itsykson, P., Turetsky, T., Pera, M. F., Reinhartz, E., Itzik, A., and Ben-Hur, T. 2001. Neural progenitors from human embryonic stem cells. *Nat Biotechnol* 19:1134-1140.
5. Itsykson, P., Ilouz, N., Turetsky, T., Goldstein, R. S., Pera, M. F., Fishbein, I., Segal, M., and Reubinoff, B. E. 2005. Derivation of neural precursors from human embryonic stem cells in the presence of noggin. *Mol Cell Neurosci* 30:24-36.
6. Li, X. J., Du, Z. W., Zarnowska, E. D., Pankratz, M., Hansen, L. O., Pearce, R. A., and Zhang, S. C. 2005. Specification of motoneurons from human embryonic stem cells. *Nat Biotechnol* 23:215-221.
7. Lee, H., Shamy, G. A., Elkabetz, Y., Schofield, C. M., Harrsion, N. L., Panagiotakos, G., Socci, N. D., Tabar, V., and Studer, L. 2007. Directed differentiation and transplantation of human embryonic stem cell-derived motoneurons. *Stem Cells* 25:1931-1939.
8. Li, X. J., Hu, B. Y., Jones, S. A., Zhang, Y. S., Lavaute, T., Du, Z. W., and Zhang, S. C. 2008. Directed Differentiation of Ventral Spinal Progenitors and Motor Neurons from Human Embryonic Stem Cells by Small Molecules. *Stem Cells.*
9. Nistor, G. I., Totoiu, M. O., Hague, N., Carpenter, M. K., and Keirstead, H. S. 2005. Human embryonic stem cells differentiate into oligodendrocytes in high purity and myelinate after spinal cord transplantation. *Glia* 49:385-396.
10. Izrael, M., Zhang, P., Kaufman, R., Shinder, V., Ella, R., Amit, M., Itskovitz-Eldor, J., Chebath, J., and Revel, M. 2007. Human oligodendrocytes derived from embryonic stem cells: Effect of noggin on phenotypic differentiation in vitro and on myelination in vivo. *Mol Cell Neurosci* 34:310-323.
11. Billon, N., Jolicoeur, C., Ying, Q. L., Smith, A., and Raff, M. 2002. Normal timing of oligodendrocyte development from genetically engineered, lineage-selectable mouse ES cells. *J Cell Sci* 115:3657-3665.
12. Lowell S, Benchoua A, Heavey B, Smith A G. Notch promotes neural lineage entry by pluripotent embryonic stem cells. PLoS Biol. 2006 May; 4(5):e121. Epub 2006 Apr. 11
13. Dovey et al., 2001, J. Neurochem 76:173-181
14. Fortini Nature Reviews Molecular Cell Biology 3, 673-684 (2002)
15. Wang S et al., Notch receptor activation inhibits oligodendrocyte differentiation. Neuron 21 63-75 (1998)
16. Givogri M I et al., Central nervous system myelination in mice with deficient expression of Notch1. J Neurosci Res. (2002) February 1; 67(3):309-20.
17. John et al., Multiple sclerosis: re-expression of a developmental pathway that restricts oligodendrocyte maturation. Nature Medicine 8:1115; (2002).
18. International Patent Application Publication No. WO 04/090110;
19. International Patent Application Publication No. WO 06/095175

The invention claimed is:

1. A method for directing terminal differentiation of neural precursors into motor neurons comprising:

providing a population of neural precursors;

culturing the neural precursors in a first culturing medium comprising a basic medium supplemented with at least hedgehog (HH) or an HH agonist and with retinoic acid (RA) to obtain neural progenitors having a caudal and ventral specification that is exhibited by at least expression of Ngn2$^+$;

after obtaining the neural progenitors having a caudal and ventral specification, culturing the neural progenitors having a caudal and ventral specification in a second culturing medium comprising a basic medium supplemented with at least one inhibitor of the Notch signaling pathway, and allowing the neural progenitors having a caudal and ventral specification to terminally differentiate into postmitotic motor neurons expression HB9.

2. The method of claim 1, wherein the neural precursors are developed from stem cells.

3. The method of claim 2, wherein the stem cells are pluripotent stem cells.

4. The method of claim 3, wherein the pluripotent stem cells are human stem cells selected embryonic stem cells or induced pluripotent stem cells (iPS cells).

5. The method of claim 1, wherein the neural cells are spheres enriched with neural precursors, wherein the spheres comprise at least 35% neural precursors.

6. The method of claim 2, wherein the neural precursors are characterized by the expression of at least one cellular marker selected from the group consisting of Pax6 and nestin.

7. The method of claim 1, wherein the HH is a Sonic HH (SHH) agonist.

8. The method of claim 7, wherein the SHH agonist is selected from the group consisting of purmorphamine (Pur) and Hh-Ag1.3.

9. The method of claim 1, wherein the first culturing medium comprises between about 0.5 µM to 2.0 µM of the HH or HH agonist.

10. The method of claim 1, wherein the first culturing medium comprises between 0.5 µM to 20 µM RA.

11. The method of claim 1, wherein the first culturing medium comprises 0.5 µM SHH agonist and 1 µM RA.

12. The method of claim 1, wherein the culturing in the first culturing medium is carried out for between about 1 to 3 weeks.

13. The method of claim 1, wherein the at least one inhibitor of the Notch signaling pathway comprises an inhibitor of the ν-secretase complex.

14. The method of claim 13, wherein the inhibitor of the ν-secretase complex is N-(3,5-Difluorophenacetyl)-L-alanyl]-S-phenylglycine t-butyl ester (DAPT).

15. The method of claim 1, wherein the culturing in the culturing medium comprising the inhibitor is carried out for between about 7 to 14 days.

16. The method of claim 1, wherein the propagating comprises culturing the neural progenitors in an intermediate culturing medium comprising a basic medium supplemented with N2 serum replacement, a member of dibutyryl cyclic AMP, glial cell derived neurotrophic factors (GDNF), BDNF, and IGF-I.

17. The method of claim 1, wherein the propagating is carried out for between 2 to 20 weeks.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Homo sapiens

<400> SEQUENCE: 1
tcagaaggag acggaggcta                                              20

<210> SEQ ID NO 2
<211> LENGTH: 20
<212> TYPE: DNA
<213> ORGANISM: Homo sapiens

<400> SEQUENCE: 2
agctgccttg tggtgaagtt                                              20

<210> SEQ ID NO 3
<211> LENGTH: 20
<212> TYPE: DNA
<213> ORGANISM: Homo sapiens

<400> SEQUENCE: 3
aagtgctcca ctccggtcta                                              20

<210> SEQ ID NO 4
<211> LENGTH: 20
<212> TYPE: DNA
```

```
<213> ORGANISM: Homo sapiens

<400> SEQUENCE: 4
gctgagcagt ttgctctcct                                               20

<210> SEQ ID NO 5
<211> LENGTH: 20
<212> TYPE: DNA
<213> ORGANISM: Homo sapiens

<400> SEQUENCE: 5
gacgggttag acagccaaag                                               20

<210> SEQ ID NO 6
<211> LENGTH: 20
<212> TYPE: DNA
<213> ORGANISM: Homo sapiens

<400> SEQUENCE: 6
gcctctagga ccacttgctg                                               20

<210> SEQ ID NO 7
<211> LENGTH: 20
<212> TYPE: DNA
<213> ORGANISM: Homo sapiens

<400> SEQUENCE: 7
ctcaggctac cagcagaacc                                               20

<210> SEQ ID NO 8
<211> LENGTH: 20
<212> TYPE: DNA
<213> ORGANISM: Homo sapiens

<400> SEQUENCE: 8
cttcaatccg acgttttcgt                                               20

<210> SEQ ID NO 9
<211> LENGTH: 20
<212> TYPE: DNA
<213> ORGANISM: Homo sapiens

<400> SEQUENCE: 9
gctgtggaaa cagtttgggt                                               20

<210> SEQ ID NO 10
<211> LENGTH: 20
<212> TYPE: DNA
<213> ORGANISM: Homo sapiens

<400> SEQUENCE: 10
aagggtgtta cacggcagac                                               20

<210> SEQ ID NO 11
<211> LENGTH: 20
<212> TYPE: DNA
<213> ORGANISM: Homo sapiens

<400> SEQUENCE: 11
caagaaacag cgagagggag                                               20

<210> SEQ ID NO 12
<211> LENGTH: 20
<212> TYPE: DNA
```

-continued

```
<213> ORGANISM: Homo sapiens

<400> SEQUENCE: 12
aacgctcgtg acataatccc                                           20

<210> SEQ ID NO 13
<211> LENGTH: 24
<212> TYPE: DNA
<213> ORGANISM: Homo sapiens

<400> SEQUENCE: 13
tagagctgcc atttctgcta ccca                                      24

<210> SEQ ID NO 14
<211> LENGTH: 24
<212> TYPE: DNA
<213> ORGANISM: Homo sapiens

<400> SEQUENCE: 14 cgccacccttt ggctttgaca ataa                                     24

<210> SEQ ID NO 15
<211> LENGTH: 20
<212> TYPE: DNA
<213> ORGANISM: Homo sapiens

<400> SEQUENCE: 15
ctgtgctgaa cgagaagcag                                           20

<210> SEQ ID NO 16
<211> LENGTH: 20
<212> TYPE: DNA
<213> ORGANISM: Homo sapiens

<400> SEQUENCE: 16
tttccaaggt ggctggtaac                                           20

<210> SEQ ID NO 17
<211> LENGTH: 20
<212> TYPE: DNA
<213> ORGANISM: Homo sapiens

<400> SEQUENCE: 17
agccacatcg ctcagacacc                                           20

<210> SEQ ID NO 18
<211> LENGTH: 19
<212> TYPE: DNA
<213> ORGANISM: Homo sapiens

<400> SEQUENCE: 18
gtactcagcg ccagcatcg                                            19
```